United States Patent
Renze et al.

(10) Patent No.: US 7,067,689 B1
(45) Date of Patent: Jun. 27, 2006

(54) PROCESS FOR PRODUCTION OF PENTAHYDROXYHEXYLCARBAMOYL ALKANOIC ACIDS

(75) Inventors: Juergen T. Renze, Jamaica Plain, MA (US); John J. Talley, Somerville, MA (US)

(73) Assignee: Microbia, Inc., Cambridge, MA (US)

( * ) Notice: Subject to any disclaimer, the term of this patent is extended or adjusted under 35 U.S.C. 154(b) by 0 days.

(21) Appl. No.: 11/177,410

(22) Filed: Jul. 8, 2005

(51) Int. Cl.
*C07C 229/00* (2006.01)

(52) U.S. Cl. .................................. 560/170

(58) Field of Classification Search ............... None
See application file for complete search history.

(56) References Cited

U.S. PATENT DOCUMENTS

2005/0020563 A1   1/2005   Jaehne et al. .......... 514/210.02

FOREIGN PATENT DOCUMENTS

WO    WO 2004/087655    10/2004

OTHER PUBLICATIONS

Prata, et al., "Charge-Reversal Amphiphiles for Gene Delivery", *J. Am. Chem. Soc.* 126, 1296-12197 (2004).
Saitoh, et al., "Convenient Selective Monoesterification of α, ω-Dicarboxylic Acids Catalyzed by Ion-Exchange Resins", *Tetrahedron Letters*, 37, 6733-6736 (1996).

*Primary Examiner*—Paul A. Zucker
(74) *Attorney, Agent, or Firm*—Heslin Rothenberg Farley & Mesiti, P.C.; Philip E. Hansen

(57) ABSTRACT

The present invention relates to improved processes for the production of compounds of formula I:

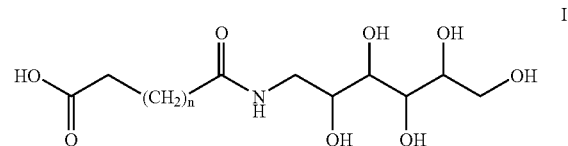

11 Claims, No Drawings

PROCESS FOR PRODUCTION OF PENTAHYDROXYHEXYLCARBAMOYL ALKANOIC ACIDS

FIELD OF THE INVENTION

The present invention relates to processes for the production of pentahydroxyhexylcarbamoyl alkanoic acids.

BACKGROUND OF THE INVENTION

A process for the preparation of pentahydroxyhexylcarbamoyl undecanoic acid is disclosed in U.S. patent application Publication No. 2005/0020563. That process provides an overall yield of only 29% final product. A process that affords a higher overall yield for the preparation of pentahydroxyhexylcarbamoyl undecanoic acid (and other alkanoic acids) would be desirable.

SUMMARY OF THE INVENTION

The present invention relates to a process for preparing pentahydroxyhexylcarbamoyl alkanoic acids,

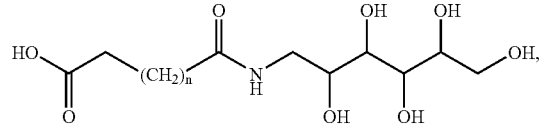

particularly, pentahydroxyhexylcarbamoyl undecanoic acid, the compound of formula Ia:

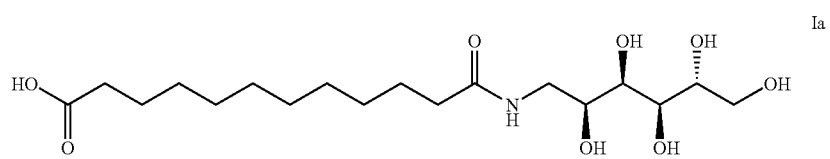

In a first aspect, the invention relates to a process for preparing a compound of formula I:

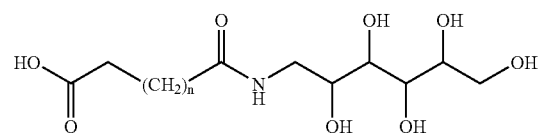

wherein n is an integer from 6 to 17 comprising the steps of:

a) reacting a monoester of a dioic acid of formula

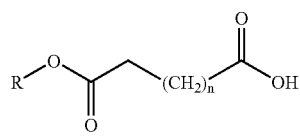

with 2,3,4,5,6-pentahydroxyhexylamine to form an ester/amide of formula

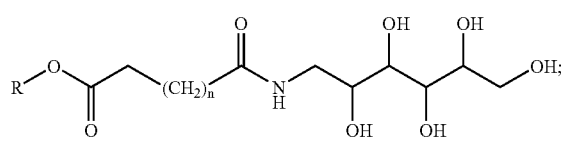

b) reacting the ester/amide with a reagent to cleave the ester functionality and provide a compound of formula I c) optionally isolating pentahydroxyhexylcarbamoyl alkanoic acid.

The monoester of a dioic acid of formula

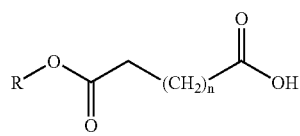

may be obtained by reacting an alkanedioic acid with benzyl formate, a formate ester of substituted benzyl alcohol, allyl formate, 2-(trimethylsilyl)ethyl formate, or 9-fluorenylmethyl formate in the presence of an acid catalyst. R is chosen from benzyl, substituted benzyl, allyl, 2-(trimethylsilyl)ethyl, and 9-fluorenylmethyl.

In another aspect, the invention relates to chemical compounds of formula

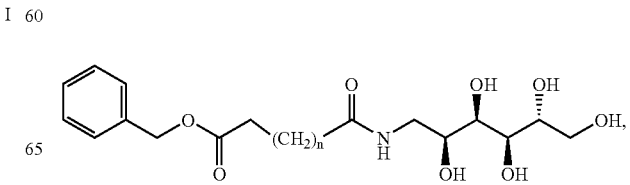

particularly compound IIa:

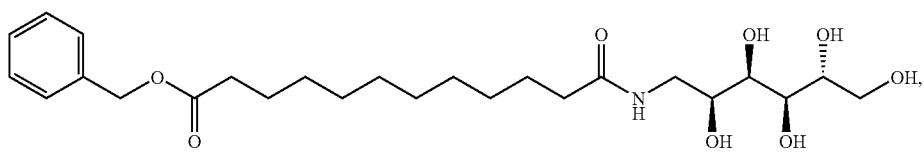

which are useful as intermediates in the process of the invention.

DETAILED DESCRIPTION OF THE INVENTION

Throughout this application, various references are cited. The disclosures of each of these publications in their entireties are hereby incorporated by reference as if written herein.

In its broadest sense, the present invention provides a process for preparing the compound of formula I:

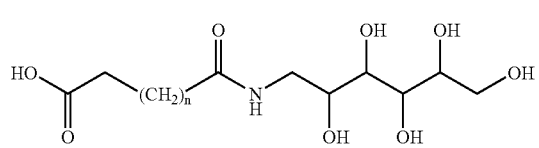

According to the process of the invention, a dioic acid monoester of formula

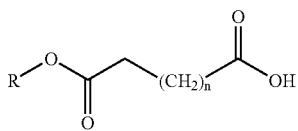

is reacted with 2,3,4,5,6-pentahydroxyhexylamine to form an ester/amide of formula

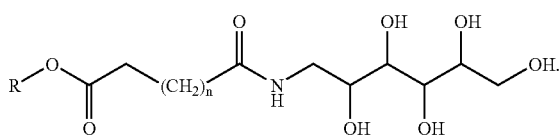

In this process, R is a protecting group for a carboxylic acid, and it is chosen from benzyl, substituted benzyl, allyl, 2-(trimethylsilyl)ethyl, and 9-fluorenylmethyl. These groups are then removed using the appropriate reagent to provide the corresponding acid, I. When R is benzyl or substituted benzyl (e.g. methoxybenzyl), the preferred reagent for cleaving the protecting group is a noble metal catalyst, such as a platinum or palladium catalyst, for example Pd(0) on carbon, in the presence of a source of hydrogen. When R is allyl, the preferred reagent for cleaving the protecting group is a palladium catalyst, for example Pd(Ph$_3$P)$_4$ in the presence of a secondary amine, such as morpholine [see Friedrich-Bochnitschek, S.; Waldmann, H.; Kunz, H. *J. Org. Chem.* 1989, 54, 751]. When R is 2-(trimethylsilyl)ethyl, the preferred reagent for cleaving the protecting group is fluoride ion, e.g. tetrabutylammonium fluoride [see Siever, P. *Helv. Chim. Acta.* 1977, 60, 2711]. When R is 9-fluorenylmethyl, the preferred reagent for cleaving the protecting group is piperidine or diethylamine [see Kessler, H.; Siegmeier, R. *Tetrahedron Lett.* 1983, 24, 281]. Other reagents and conditions for attaching and cleaving the aforementioned protecting groups may be found in Greene and Wuts *Protective Groups in Organic Synthesis* Second Edition John Wiley & Sons, New York 1991, pages 224–263.

The reagents and conditions for formation of an amide from an acid and an amine are well known to one with skill in the art. Reagents and methods useful in the preparation include carbodiimides of various sorts, mixed anhydrides, EEDQ, HATU, and the like. It is also possible to pre-react the carboxylic acid with an appropriate leaving group to form an activated ester. Activated esters denote esters which are capable of undergoing a substitution reaction with primary or secondary amines to form an amide. The term includes esters "activated" by neighboring electron withdrawing substituents. Examples include esters of phenols, particularly electronegatively substituted phenol esters such as pentafluorophenol esters; O-esters of isourea, such as arise from interaction with carbodiimides; O-esters of N-hydroxyimides and N-hydroxy heterocycles; specific examples include S-t-butyl esters, S-phenyl esters, S-2-pyridyl esters, N-hydroxypiperidine esters, N-hydroxysuccinimide esters, N-hydroxyphthalimide esters and N-hydroxybenzotriazole esters. Other methods for generating amides may be found in standard synthetic chemistry texts, including "Organic Functional Group Preparations", 2$^{nd}$ ed., Sandier and Wolf, eds. 1983, pp 315–358; incorporated herein by reference. In an embodiment described below, the condensation is accomplished using a carbodiimide and an N-hydroxy heterocycle.

In one embodiment the process for preparing compound Ia comprises the steps of:
 a) reacting a benzyl monoester of dodecanedioic acid with D-glucamine under conditions for forming an amide;
 b) hydrogenolyzing said amide.

The process optionally further comprises the step of: isolating a compound of formula Ia.

In some embodiments the monoester of dodecanedioic acid is monobenzyl dodecanedioate,

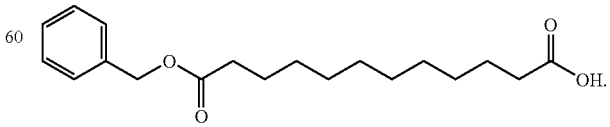

and the resulting amide is a compound having chemical formula IIA, as shown below:

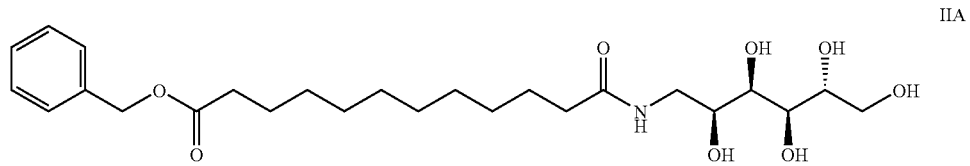

IIA

Following synthesis of the monoester, the benzyl is hydrogenolyzed under conditions appropriate to produce the corresponding compound of formula I having a free carboxylic acid. This step is illustrated below, in scheme 2:

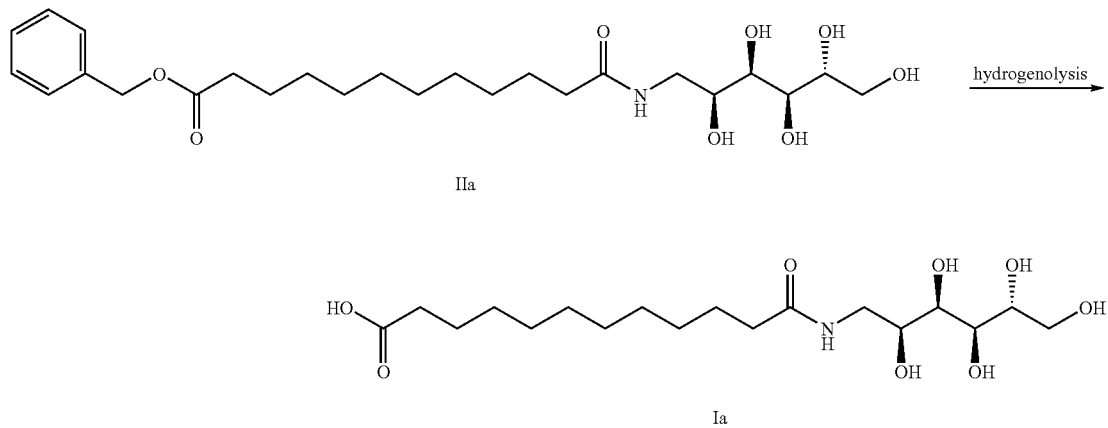

In one embodiment, monobenzyl dodecanedioate is prepared by reacting benzyl formate with dodecanedioic acid in the presence of a strong acid ion exchange resin according to a process as shown in scheme 3, herein below:

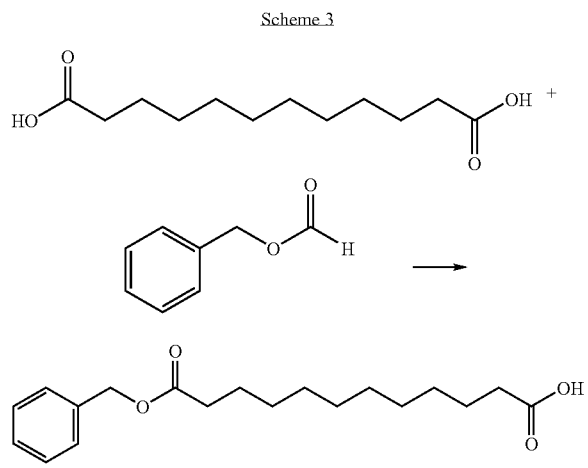

While any acid would, in principle, catalyze the transesterification of formate with the dicarboxylic acid, strong acid ion exchange resins offer the advantage of being easily removed from the reaction when it is complete. Strong acid ion exchange resins are generally sulfonated divinyl benzene polymers. Many are commercially available, such as AMBERLITE IR-118®, AMBERLITE IR-120® and AMBERLYST 15® from Rohm & Haas and the DOWEX 50® series resins from Dow Chemical.

Other methods of synthesizing monobenzyl esters of dodecanedioic acid are known, but do not appear to have the selectivity for the monoester that is seen in the formate ester exchange reaction. For example, monoesters may be prepared according to the following illustrative methods: esterification of an acid in the presence of dicyclohexylcarbodiimide (DCC), 4-dimethylaminopyridine (DMAP) and benzyl alcohol (Neises, B.; Andries, T.; Steglich, W. *J. Chem Soc., Chem. Commun.* 1982, 1132); reaction of an acid with N,N-dimethylformamide dibenzyl acetal (Emmer, G.; Grassberger, M. A.; Meingassner, J. G.; Schultz, G.; Schaude, M. *J. Med. Chem.* 1994, 37, 1908); reaction of an acetonitrile solution of an acid with benzyl bromide in the presence of 1,8-diazabicyclo[5.4.0]undec-7-ene (DBU) (Smith, M. J.; Kim, D.; Horenstein, B.; Nakanishi, K.; Kustin, K. *Acc. Chem. Res.* 1991, 24, 117).

Other routes to other monoesters of dodecanedioic acid may also be employed. These methods include the synthesis of a mono-allyl ester of dodecanedioic acid, from allyl formate and dodecandioic acid; mono-[2-(trimethylsilyl)ethyl] ester dodecanedioic acid, from 2-trimethylsilylethyl formate and dodecanedioic acid; mono-4-methoxybenzyl ester dodecanedioic acid, from 4-methoxybenzyl formate and dodecandioic acid; and mono-9-fluorenylmethyl ester dodecanedioic acid, from 9-fluorenylmethyl formate and dodecandioic acid.

Also within the scope of the invention are compounds useful as intermediates in the process described herein. The generic intermediate is:

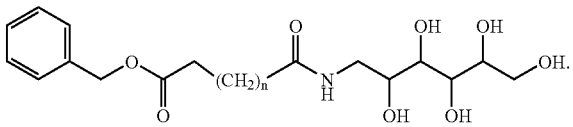

A specific intermediate has chemical formula as shown below:

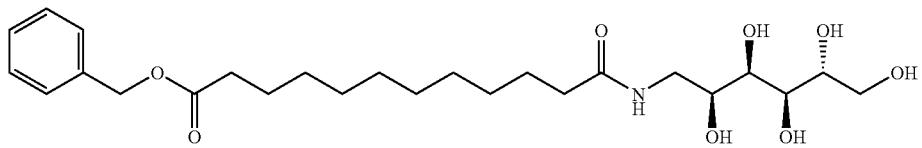

IIa

Definitions

In this specification the terms and substituents are defined when introduced and retain their definitions throughout.

Alkyl is intended to include linear, branched, or cyclic hydrocarbon structures and combinations thereof. When not otherwise restricted, the term refers to alkyl of 20 or fewer carbons. Lower alkyl refers to alkyl groups of 1, 2, 3, 4, 5 and 6 carbon atoms. Examples of lower alkyl groups include methyl, ethyl, propyl, isopropyl, butyl, s-and t-butyl and the like. Preferred alkyl and alkylene groups are those of $C_{20}$ or below (e.g. $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$)—Cycloalkyl is a subset of alkyl and includes cyclic hydrocarbon groups of 3, 4, 5, 6, 7, and 8 carbon atoms. Examples of cycloalkyl groups include c-propyl, c-butyl, c-pentyl, norbornyl, adamantyl and the like.

Alkoxy or alkoxyl refers to groups of 1, 2, 3, 4, 5, 6, 7 or 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Polyol refers to a compound or residue having a plurality of —OH groups. Polyols may be thought of as alkyls in which a plurality of C—H bonds have been replaced by C—OH bonds. Common polyol compounds include for example glycerol, erythritol, sorbitol, xylitol, mannitol and inositol. Linear polyol residues will generally be of the empirical formula —$C_yH_{2y+1}O_y$, and cyclic polyol residues will generally be of the formula —$C_yH_{2y-1}O_y$. Those in which y is 3, 4, 5 and 6 are preferred. Cyclic polyols also include reduced sugars, such as glucitol.

Reduced amine sugars include D-glucamine, also known in the art as 1-amino-1-deoxy-D-glucitol and (2R,3R,4R,5S)-6-aminohexane-1,2,3,4,5-pentol.

Acyl refers to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Arylalkyl means an alkyl residue attached to an aryl ring. Examples are benzyl, phenethyl and the like.

Substituted benzyl refers to benzyl residues in which the benzyl carries substituents that modulate cleavage. Well known examples include methoxybenzyl, bromobenzyl, 2,4,6-trimethylbenzyl, trityl and diphenylmethyl.

The term "halogen" means fluorine, chlorine, bromine or iodine.

Terminology related to "protecting", "deprotecting" and "protected" functionalities occurs throughout this application. Such terminology is well understood by persons of skill in the art and is used in the context of processes, which involve sequential treatment with a series of reagents. In that context, a protecting group refers to a group that is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere.

The abbreviations Me, Et, Ph, Tf, Ts and Ms represent methyl, ethyl, phenyl, trifluoromethanesulfonyl, toluensulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The graphic representations of racemic, ambiscalemic and scalemic or enantiomerically pure compounds used herein are taken from Maehr *J. Chem. Ed.* 62 114–120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. The compound of formula Ia was synthesized by coupling D-glucamine [(2R,3R,4R,5S)-6-aminohexane-1,2,3,4,5-pentol]

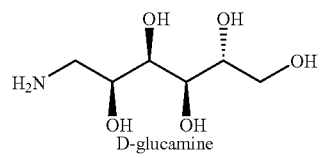
D-glucamine to monobenzyl dodecanedioate. Thus, the formula Ia is intended to encompass the pure enantiomer:

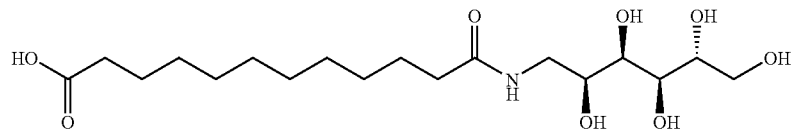

The term "enantiomeric excess" is well known in the art and is defined for a resolution of ab into a+b as $$ee_a = \left(\frac{\text{conc. of } a - \text{conc. of } b}{\text{conc. of } a + \text{conc. of } b}\right) \times 100$$

The term "enantiomeric excess" is related to the older term "optical purity" in that both are measures of the same phenomenon. The value of ee will be a number from 0 to 100, zero being racemic and 100 being pure, single enantiomer. A compound which in the past might have been called 98% optically pure is now more precisely described as 96% ee; in other words, a 90% ee reflects the presence of 95% of one enantiomer and 5% of the other in the material in question.

EXAMPLES

Abbreviations: The following abbreviations and terms have the indicated meaning throughout, unless otherwise stated:

| | |
|---|---|
| Ac | acetyl |
| AcOH | Acetic acid |
| Boc | tert-butoxycarbonyl |
| Boc$_2$O | tert-butoxycarbonic anhydride |
| Bu | butyl |
| C | carbon |
| c | cyclo |
| CDCl$_3$ | Deuterated chloroform |
| CD$_3$OD | Deuterated methanol |
| δ | NMR chemical shift referenced to tetramethylsilane |
| DCE | 1,2-dichloroethane |
| DCM | dichloromethane = methylene chloride = CH$_2$Cl$_2$ |
| DIC | Diisopropyl carbodiimide |
| DIPEA | Diisopropylethylamine |
| DMAP | 4-Dimethylamino pyridine |
| DMF | N,N-dimethylformamide |
| DMSO | Dimethyl sulfoxide |
| EDC | (N-(3-dimethylaminopropyl)-N'-ethylcarbodiimide hydrochloride) |
| Et | Ethyl |
| EtOAc | Ethyl acetate |
| Et$_3$N | Triethylamine |
| Et$_3$SiH | Triethylsilane |
| $^1$H NMR | Proton Nuclear Magnetic Resonance |
| h | hours |
| Hexanes | HPLC grade isomeric hexanes |
| HOBt | hydroxybenzotriazole |
| i | iso |
| LCMS | Liquid Chromatography Mass Spectroscopy |
| m- | meta |
| Me | methyl |
| MeOH | methanol = CH$_3$OH |
| min | minutes |
| n | normal |
| N | nitrogen |
| NMR | Nuclear Magnetic Resonance |
| NaBH$_4$ | sodium borohydride |
| NaCNBH$_3$ | sodium cyano borohydride |
| Na(OAc)$_3$BH | sodium triacetoxy borohydride |
| o- | ortho |
| p- | para |
| Ph | Phenyl |
| r.t. | room temperature |
| sat'd | saturated |
| s | secondary |
| t | tertiary |
| TFA | trifluoro acetic acid |
| THF | tetrahydrofuran |

Chemical Synthesis

In general, the process of the present invention may be carried out according to the description in the general reaction schemes as, for example, described below, or by modifications thereof that make use of variants that are in themselves known, but are not mentioned here. The starting materials, for example are either commercially available, synthesized as described in the examples or may be obtained by the methods well known to persons of skill in the art. The following examples will further describe the invention, and are used for the purposes of illustration only, and should not be considered as limiting the invention being disclosed.

Example 1

Process for the preparation of 1-[(11-carboxyundecanoyl)amino]-1-deoxy-D-glucitol The following is a description of an efficient method for the preparation of the compound of formula Ia in overall yield of 74% from commercially available starting materials. In comparison, the procedure for the preparation of the compound of formula Ia described in WO 2004/087655 afforded an overall yield of 29%.

Dodecanedioic diacid (1 mmol) and Dowex 50W-X2 (50–100 mesh) (1.0 g) are stirred in benzyl formate/octane (2:8, 10 mL) at 80° C. for 12 hours. The solution is filtered and the filtrate evaporated. The crude produce is purified by column chromatography on silica gel eluting with 1:4 ethyl acetate/hexanes to afford monobenzyl dodecanedioate as a white power (79% yield). $^1$H NMR (CDCl$_3$) δ ppm 1.34 (m, 10H, (CH$_2$)$_n$), 1.61 (m, 4H, CH$_2$), 2.32 (m, 4H, CH$_2$), 5.08 (s, 2H, CH$_2$), 7.34 (m, 5H, Ph); $^{13}$C NMR (CDCl$_3$) δ ppm 25.16 (CH$_2$CH$_2$CO$_2$Ph), 25.25 (CH$_2$CH$_2$CO$_2$H), 29.40 (CH$_2$)$_n$, 29.57 (CH$_2$)$_n$, 29.71 (CH$_2$)$_n$, 34,40 (CH$_2$CO$_2$Ph), 34.62 (CH$_2$CO$_2$H), 66.55 (CO$_2$CH$_2$Ph), 127.22(Ph), 127.86 (Ph), 128.38(Ph), 128.76(Ph), 136.29(Ph), 174.04 (CO$_2$Ph), 179.73 (CO$_2$H). MH$^+$ (GC-CIMS)=321.

Monobenzyl dodecanedioate (530 mg, 1.7 mmol) was dissolved in 10 mL of DMF, to which EDC (N-(3-dimethylaminopropyl)-N'-ethylcarbodiimide hydrochloride) (325 mg, 1.7 mmol) and HOBt (1-hydroxybenzotriazole) (230 mg, 1.7 mmol) were added. The mixture was stirred at room temperature for one hour and then D-glucamine (380 mg, 1.9 mmol) was added. The mixture was stirred at room temperature overnight, poured into 50 mL water, agitated and filtered to give the desired amide, of formula IIa in 95% yield. NMR (DMSO-D-6)7.70(brm, 1H), 7.30(m, 5H), 5.07 (s, 2H), 4.73(d, 1H, J=4.5 Hz), 4.44(d, 1H, J=5.4 Hz), 4.36(d, 1H, J=6.0 Hz), 4.32 (t, 1H, J=5.7 Hz), 4.24(d, 1H, J=6.6 Hz), 3.58–3.52(m, 3H), 3.50–3.40(m, 3H), 3.21(m, 1H), 3.00(m, 1H), 2.33(t, 2H, J=7.2 Hz), 2.05(t, 2H, J=7.2 Hz), 1.50(m, 4H), 1.22(m, 12H).

The amide IIa (720 mg, 1.6 mmol) was dissolved in 70 mL of ethanol and hydrogenated at 1 atm in the presence of 0.3 g of 10% palladium on carbon for 2.5 hours to afford 643 mg of compound Ia in quantitative yield. NMR (DMSO-D-6) 7.75(brt, 1H), 4.80–4.00(brs, 5H), 3.60–3.20(m, 6H), 3.20(m, 1H), 3.00(m, 1H), 2.17(t, 2H, J=7.2 Hz), 2.05(t, 2H, J=7.2 Hz), 1.40(m, 4H), 1.22(m, 12H).

Dodecanedioic acid 4-[(2S,3R)-3-[(S)-3-(4-fluorophenyl)-3-hydroxypropyl]-2-(4-methoxyphenyl)-4-oxoazetidin-1-yl]benzylamide ((2S,3R,4R,5R)-2,3,4,5,6-pentahydroxyhexyl)amide III, of HOBt and 0.31 g (1.67 mmol) of EDC are added and the mixture is stirred at RT for 4 h. The reaction mixture is allowed to stand at RT overnight. The next morning, TLC shows complete conversion. The reaction mixture is concentrated under reduced pressure and the residue is dried under high vacuum. The residue is triturated with water (ultrasonic bath), filtered off with suction, washed with water and filtered off with suction. The crude product is recrystallized from isopropanol. The crystals are finally triturated with water, filtered off with suction and dried. This gives dodecanedioic acid 4-[(2S,3R)-3-[(S)-3-(4-fluorophenyl)-3-hydroxypropyl]-2-(4-methoxyphenyl)-4-oxoazetidin-1-yl]benzylamide ((2S,3R,4R,5R)-2,3,4,5,6-pentahydroxyhexyl)amide (III). MW: 809.97; MS: 810.49 (M+H⁺).

Although the foregoing invention has been described in some detail for purposes of illustration, it will be readily apparent to one skilled in the art that changes and modifications may be made without departing from the scope of the invention described herein.

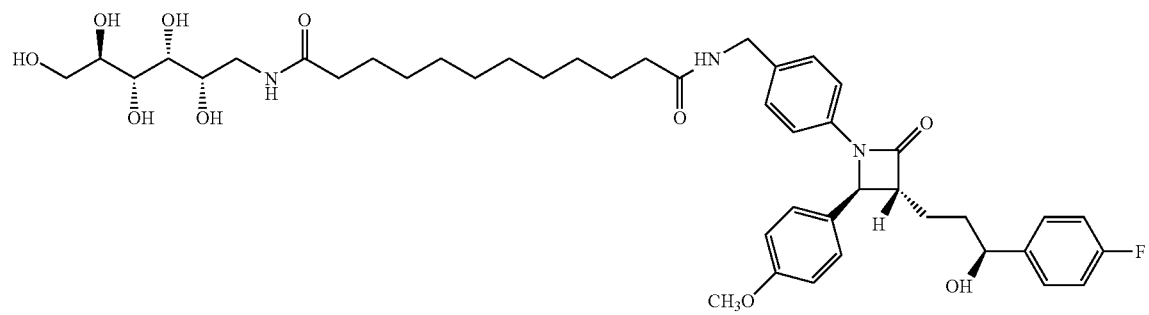

III which is described in U.S. published application 2005/0020563 as a cholesterol absorption inhibitor, may be prepared from Ia by condensing Ia with 4-[(2S,3R)-3-[(S)-3-(4-fluorophenyl)-3-hydroxypropyl]-2-(4-methoxyphenyl)-4-oxoazetidin-1-yl]benzylamine IV,

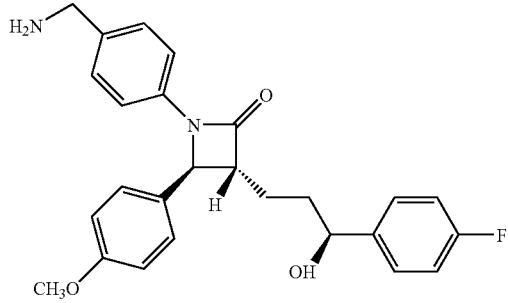

IV as described in that application:

With gentle heating, 0.63 g (1.45 mmol) of benzylamine IV (preparation see DE 10064398) and 0.65 g (1.65 mmol) of Ia are dissolved in 15 mL of dry DMF, 0.25 g (1.63 mmol)

We claim:

1. A process for preparing a compound of formula:

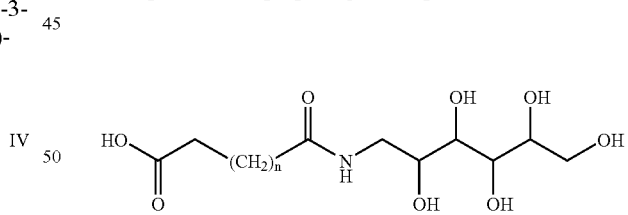

wherein n is an integer from 6 to 17 comprising the steps of:

a) reacting a monoester of a dioic acid of formula

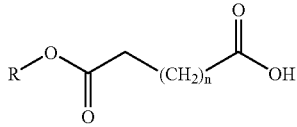

wherein R is chosen from benzyl, substituted benzyl, allyl, 2-(trimethylsilyl)ethyl, and 9-fluorenylmethyl, with 2,3,4,5,6-pentahydroxyhexylamine to form an ester/amide of formula

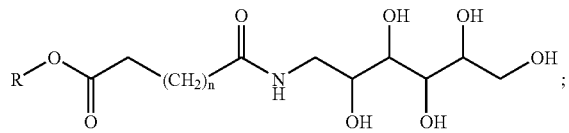

and b) reacting said ester/amide with a reagent to cleave said ester and provide said compound of formula I.

2. A process according to claim 1 wherein R is chosen from allyl, 2-(trimethylsilyl)ethyl and 9-fluorenylmethyl and said reagent for cleaving said ester is chosen from a palladium catalyst, fluoride anion and piperidine or diethylamine, respectively.

3. A process according to claim 1 comprising the steps of
a) coupling a monoester of dodecanedioic acid of formula:

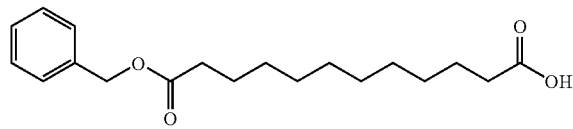

with D-glucamine to form an amide of formula Ia:

4. The process of claim 3 wherein the hydrogenolysis is carried out in the presence of a noble metal catalyst and a source of hydrogen.

5. A process according to any of claims 1–4 wherein said monoester is obtained by reacting dodecanedioic acid with a formate ester of the corresponding alcohol ROH in the presence of an acid catalyst.

6. A process according to claim 5 wherein said acid catalyst is a sulfonic acid ion exchange resin.

7. A process according to claim 6 wherein said monoester is obtained by reacting dodecanedioic acid with benzyl formate.

8. A process according to claim 7 comprising the steps of
a) reacting dodecanedioic acid with benzyl formate in the presence of a sulfonic acid ion exchange resin to provide a monoester of dodecanedioic acid of formula:

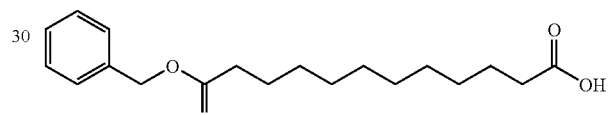

b) coupling said monoester of dodecanedioic acid

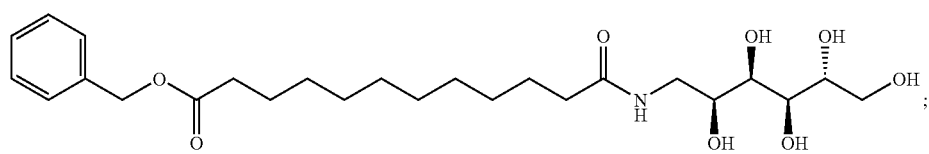

and
hydrogenolyzing the compound of formula IIA to a compound of formula Ia:

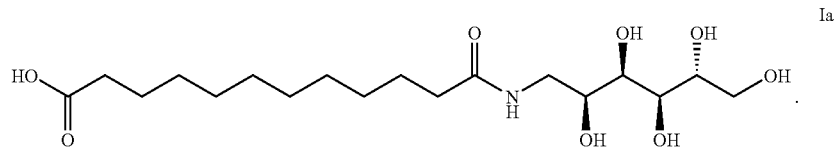

with D-glucamine to form an amide of formula Ia:

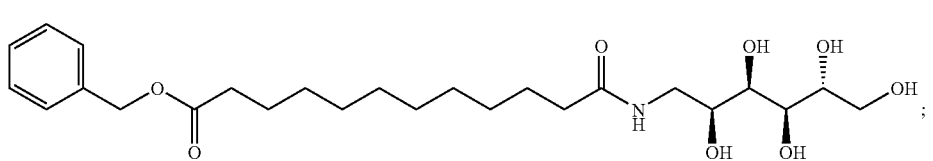

and
c) hydrogenolyzing the compound of formula IIA with palladium and hydrogen to provide a compound of formula Ia:

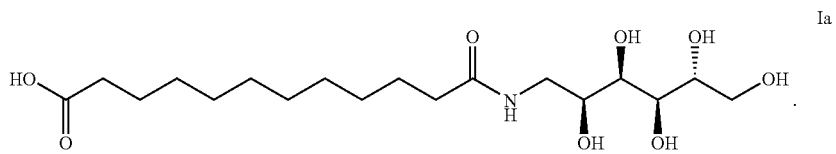

9. A process according to claim 3 for preparing dodecanedioic acid 4-[(2S,3R)-3-[(S)-3-(4-fluorophenyl)-3-hydroxypropyl]-2-(4-methoxyphenyl)-4-oxoazetidin-1-yl]benzylamide ((2S,3R,4R,5R)-2,3,4,5,6-pentahydroxyhexyl)amide comprising the additional step of condensing said compound of formula Ia with 4-[(2S,3R)-3-[(S)-3-(4-fluorophenyl)-3-hydroxypropyl]-2-(4-methoxyphenyl)-4-oxoazetidin-1-yl]benzylamine.

10. A compound of formula:

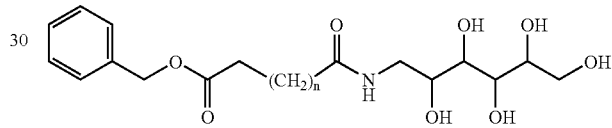

wherein n is an integer from 6 to 17.

11. A compound according to claim 10 of formula:

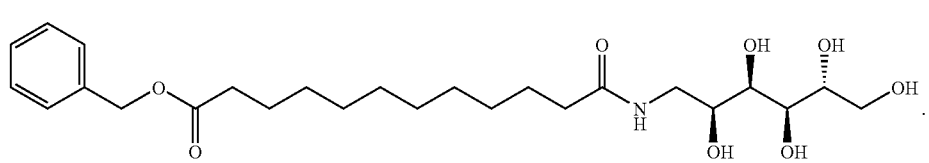

* * * * *

UNITED STATES PATENT AND TRADEMARK OFFICE
CERTIFICATE OF CORRECTION

| | |
|---|---|
| PATENT NO. | : 7,067,689 B1 |
| APPLICATION NO. | : 11/177410 |
| DATED | : June 27, 2006 |
| INVENTOR(S) | : Renze et al. |

It is certified that error appears in the above-identified patent and that said Letters Patent is hereby corrected as shown below:

Claim 3

Col.13, line 36, delete "Ia:" and insert --IIa:--

Claim 8

Col.15, line 1, delete "Ia:" and insert --IIa:--

Signed and Sealed this

Nineteenth Day of September, 2006

JON W. DUDAS
*Director of the United States Patent and Trademark Office*